United States Patent [19]

Stepp et al.

[11] Patent Number: 5,580,921
[45] Date of Patent: Dec. 3, 1996

[54] STORAGE-STABLE POLYSILOXANE COMPOSITION WHICH GIVES PERMANENTLY WATER-WETTABLE VULCANIZATES

[75] Inventors: Michael Stepp, Burghausen; Heinz Hefner, deceased, late of Burghausen, by Ursula Hefner, heiress; Peter Huber, Burghausen; Johann Mueller, Burghausen; Richard Schmidlkofer, Burghausen; Arnold Garhammer, Simbach am Inn, all of Germany

[73] Assignee: Wacker-Chemie GmbH, Munich, Germany

[21] Appl. No.: 196,106

[22] PCT Filed: Sep. 3, 1992

[86] PCT No.: PCT/EP92/02036

§ 371 Date: Feb. 10, 1994

§ 102(e) Date: Feb. 10, 1994

[87] PCT Pub. No.: WO93/04659

PCT Pub. Date: Mar. 18, 1993

[30] Foreign Application Priority Data

Sep. 6, 1991 [DE] Germany .............. 41 29 613.3

[51] Int. Cl.⁶ ...................................... C08L 83/04
[52] U.S. Cl. .............. 524/731; 528/15; 524/264; 524/267; 524/263; 525/478
[58] Field of Search .................... 524/731, 267, 524/264, 263; 525/478; 528/15

[56] References Cited

U.S. PATENT DOCUMENTS 3,337,351  8/1967  Morehouse et al. .
3,839,388  10/1974  Nitzsche et al. .
3,933,880  1/1976  Bergstrom et al. .
4,677,161  6/1987  Suzuki et al. ............................ 524/731
4,778,832  10/1988  Futami et al. .
5,008,229  4/1991  Schuster et al. .

FOREIGN PATENT DOCUMENTS 0110370  4/1987  European Pat. Off. .
0231420  8/1987  European Pat. Off. .
1519412  5/1970  Germany .
3721784  1/1988  Germany .
3903137  8/1990  Germany .

OTHER PUBLICATIONS

"The Journal of Prosthetic Dentistry", by Barry K. Norling and Morris H. Reisbick, 42, pp. 342–347 (1979).

"Chemie und Technologie der Silicone", Verlag Chemie Weinheim, 2nd edition 1968 p. 163ff.

"Chemistry and Technology of Silicones", Academic Press, Inc., Orlando Florida 32887, 1968, p. 191ff.

"Berichte der deutschen chemischen Gesellschaft", 57, 1924, pp. 1343–1355.

*Primary Examiner*—Melvyn I. Marquis
*Attorney, Agent, or Firm*—Martin Connaughton

[57] ABSTRACT

The present invention relates to storage-stable polysiloxane compositions which give permanently water-wettable elastomers. The polysiloxane compositions of the present invention which vulcanize to yield elastomers are useful as dental impression compositions.

8 Claims, No Drawings

STORAGE-STABLE POLYSILOXANE COMPOSITION WHICH GIVES PERMANENTLY WATER-WETTABLE VULCANIZATES

Storage-stable polysiloxane composition which gives permanently water-wettable vulcanizates The present invention relates to storage-stable polysiloxane compositions which give, after vulcanization, permanently water-wettable elastomers, a process for the preparation of a hydrophilic modifier for the polysiloxane compositions, and their use as dental impression compositions.

Polysiloxane compositions which vulcanize to give elastomers are widely used as impression compositions. The addition-crosslinking systems have proved to be particularly suitable for this application, since they set faster and, in contrast to the condensation-crosslinking systems, do not require large amounts of problematical catalyst.

A considerable disadvantage of silicone impression preparations based on hydrophobic polysiloxanes is based on the fact that a precise impression of moist surfaces, such as the tissue, tooth or dental prosthesis surfaces in the oral cavity, is scarcely possible since, because of the high surface tension of water, the moisture contents try to achieve a shape with the lowest surface area. The moisture is therefore deposited in the form of drops between the surface of which an impression is to be made and the impression composition.

A surface-active impression composition causes the moisture contents to spread over the surfaces of which an impression is to be made, to form a thin film of moisture. Hollow cavities in the impression are thereby avoided, and a precise reproduction of the surface structure is achieved.

The preparation of water-wettable silicone impression compositions by mixing polysiloxane compositions with surface-active agents of relatively low molecular weight is known: the use of nonylphenoxy-poly(ethyleneoxy)ethanol is described in K. B. Norling, M. H. Reisbick; The Journal of Prosthetic Dentistry 42, 342–347 (1979), the use of proteins, hydrophilic silicone oils and nonionic surface-active agents is described in DE-A-37 21 784 (S. Futami and S. Terauchi; laid open on 21.1.1988 for G-C Dental Industrial Corp., Tokyo, JP), and the use of siloxane components having alkylene ether groups in polysiloxane compositions is described in EP-A-231 420 (H. Gribi; laid open on 12.8.1987 for Dentsply GmbH, Konstanz, DE ).

The above impression compositions have the disadvantage that the surface-active agents sometimes have a tendency to demix from the impression compositions, migrate to the surface thereof or are extracted in contact with aqueous media due to the poor bonding in the impression compositions. In the last case, the water-wettability is lost by, for example, rinsing with water, disinfection, sterilization or production of duplicates with the aid of impression preparations containing water, such as gypsum, before the desired application aims, such as reproducible wetting properties of the silicone impression after removal from the moist surface, are achieved.

Organosiloxane/alkylene ether copolymers dissolved in water or in a water-soluble organic solvent are known as anti-fogging agents from DE-A 1 519 412 (E. L. Morehouse; laid open on 21.5.1970 for Union Carbide Corp., New York, U.S.A. ), it being possible for the copolymers to contain aliphatic double bonds or Si—H groups.

According to the preparation process described therein, alkylene ether groups containing allyl end groups are reacted with dichloromethylsilane in a hydrosilylation reaction in the presence of a platinum catalyst. The product is then hydrolyzed with silanes containing vinyl groups, Si—H groups and chlorine and methyl groups to give the copolymers.

The bonding of polyether units to one of the components of the polysiloxane base composition, inter alia, is proposed for silicone impression compositions in EP-A-231 420. Permanently water-wettable vulcanizates can be obtained by the polyether units being crosslinked in.

However, the siloxane components having alkylene ether groups which are described in EP-A-231 420 and which improve the wettability and can be mixed with the polysiloxane composition, and the polysiloxanes having alkylene ether units which are described in DE-A-1 519 412, and which can be crosslinked into the polysiloxane composition as hydrophilic modifiers, have a content of noble metal catalyst resulting from their preparation. In addition, the hydrophilic modifiers containing double bonds which it has hitherto been possible to prepare contain small amounts of Si—H groups, and the hydrophilic modifiers containing Si—H groups which it has hitherto been possible to prepare contain small amounts of double bonds.

Because of the deficiencies described above, when the known copolymers are used as hydrophilic modifiers, they do not give storage-stable mixtures either with the two-component rubber component (A), which comprises a polysiloxane composition having aliphatic double bonds and a noble metal catalyst, or with component (B), which comprises a polysiloxane composition having Si—H groups. In all cases, vulcanizate contents form during storage.

Separate storage of the hydrophilic modifier is not a satisfactory solution, since a three-component polysiloxane composition is difficult to handle when used in practice.

The present invention is based on the object of providing polysiloxane compositions which give permanently water-wettable elastomeric vulcanizates, the two components of the compositions being stable towards premature vulcanization during storage.

The invention relates to a storage-stable polysiloxane composition which gives permanently water-wettable elastomeric vulcanizates and consists of the components (A) which comprises a polysiloxane composition having aliphatic double bonds and a noble metal catalyst, and (B) which comprises a polysiloxane composition having Si—H groups and if appropriate additionally aliphatic double bonds, a hydrophilic modifier which is free from noble metal catalysts and comprises a (poly)siloxane matrix having alkylene ether units bonded chemically to the (poly)siloxane matrix and i) radicals having aliphatic double bonds being contained in component (A), and/or ii) Si—H groups and/or radicals having aliphatic double bonds being contained in component (B).

In the two-component systems which can be used according to the invention, the noble metal catalyst required for the vulcanization is mixed into the polysiloxane composition of component (A). Even if component (B) and the catalyst formulation used contain no aliphatic double bonds, no polysiloxane composition of satisfactory storage stability can be obtained if component (B) also comprises the catalyst. Residues of moisture, which are introduced, for example, by fillers or modifiers, with Si—H groups and catalyst leads to the evolution of hydrogen.

A hydrophilic modifier containing Si—H groups therefore also can be mixed only into component (B) for storage. The hydrophilic modifier which contains Si—H groups and is prepared according to the invention gives a storage-stable component (B).

The hydrophilic modifier containing aliphatic double bonds which is prepared according to the invention can also be mixed into component (B), since it is free from a noble metal catalyst. In this case, a content of aliphatic double bonds in component (B) causes no trouble. However, the hydrophilic modifier can also be mixed into component (A) if it is free from Si—H groups. Storage-stable components for the polysiloxane composition according to the invention can thus be prepared with the hydrophilic modifier containing aliphatic double bonds.

The storage-stable polysiloxane composition according to the invention has a very good water-wettability both before and after vulcanization. The wettability of the vulcanizates also remains practically unchanged after relatively long contact with aqueous systems, for example after sterilization.

Preferably, the hydrophilic modifier contains exclusively radicals having aliphatic double bonds, and is contained both in component (B) and in component (A). In this embodiment, the total amount of hydrophilic modifier in the storage-stable polysiloxane composition, and hence the hydrophilic properties, can be increased considerably without demixing occurring.

Another advantage of this embodiment is that the hydrophilic modifier can be present homogeneously and in the same concentration in both components. This is of great importance when using modern application forms, such as double-chamber cartridges with an attached static mixer, due to the very short mixing times.

In the preferred polysiloxane composition according to the invention, the hydrophilic modifier has the general formula I

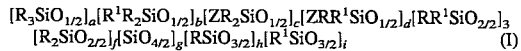

$$[R_3SiO_{1/2}]_a[R^1R_2SiO_{1/2}]_b[ZR_2SiO_{1/2}]_c[ZRR^1SiO_{1/2}]_d[RR^1SiO_{2/2}]_3$$
$$[R_2SiO_{2/2}]_f[SiO_{4/2}]_g[RSiO_{3/2}]_h[R^1SiO_{3/2}]_i \qquad (I)$$

in which the radicals

R denote hydrogen atoms or identical or different monovalent, optionally halogen-substituted $C_1$–$C_{12}$-hydrocarbon radicals bonded via SiC, in which at least one of the radicals R contains an aliphatic double bond or denotes a hydrogen atom;

$R^1$ denotes the general formula II

$$E[OY]_xR^2 \qquad (II)$$

in which E denotes a single bond or a $C_1$–$C_6$-alkylene radical, Y denotes identical or different $C_1$–$C_4$-alkylene radicals, $R^2$ denotes a hydroxyl group or a $C_1$–$C_6$-alkoxy or $C_1$–$C_6$-oxycarbonylalkyl radical and x has values from 1 to 20; and Z has the meanings of $R^2$ or denotes a halogen atom; with the proviso that a, b, c and d in each case independently of one another have values from 0 to 8, the sum of a+b+c+d is 2 to 8, the sum of a+b+c+d+e+f+g+h+i is 10 to 400 and the ratio of the sums of a+c+f+g+h: b+d+e+i is 100:1 to 1:1.

Examples of radicals R are alkyl radicals, such as the methyl, ethyl, n-propyl, iso-propyl, n-butyl, isobutyl, tert-butyl, n-pentyl, iso-pentyl, neo-pentyl and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, and dodecyl radicals, such as the n-dodecyl radical; cycloalkyl radicals, such as cyclopentyl, cyclohexyl and cycloheptyl radicals and methylcyclohexyl radicals; aryl radicals, such as the phenyl and the naphthyl radical; alkaryl radicals, such as o-, m- and p-tolyl radicals, xylyl radicals and ethylphenyl radicals; and aralkyl radicals, such as the benzyl radical and the alpha- and the β-phenylethyl radical.

Where appropriate, the above radicals R contain an aliphatic double bond. Examples are alkenyl radicals, such as the vinyl, allyl, 5-hexen-1-yl, E-4-hexen-1-yl, Z-4-hexen-1-yl, 2-(3-cyclohexenyl)-ethyl and cyclododeca-4,8-dienyl radical.

Examples of halogen-substituted $C_1$–$C_{12}$-hydrocarbon radicals are alkyl radicals substituted by fluorine, chlorine, bromine and iodine atoms, such as the 3,3,3-trifluoro-n-propyl radical, the 2,2,2,2',2',2'-hexafluoroisopropyl radical and the heptafluoroisopropyl radical, and halogenoaryl radicals, such as the o-, m- and p-chlorophenyl radical.

Preferred radicals R without an aliphatic double bond are the methyl and phenyl radical. Preferred radicals R with an aliphatic double bond are the vinyl, allyl and 5-hexen-1-yl radical.

The alkylene radicals are divalent straight- or branched-chain alkyl radicals which are bonded into the hydrophilic modifier via two bonds on carbon atoms of the alkyl radical.

The alkoxy radicals are straight- or branched-chain alkyl radicals bonded via an oxygen atom.

The oxycarbonylalkyl radicals are carboxylic acid radicals having a straight- or branched-chain alkyl radical.

The above examples of alkyl radicals also relate to the alkylene, alkoxy and oxycarbonylalkyl radicals explained above.

Preferred alkylene, alkoxy and oxycarbonylalkyl radicals have 1 to 3 carbon atoms.

Large values of f and small values of e and x improve the miscibility of the polysiloxane composition and hydrophilic modifier. The preferred hydrophilic modifier mixes well with components (A) and (B) and imparts a good water-wettability to the polysiloxane composition if the ratio of a+c+f+g+h: x(b+d+e+i) is 60:40 to 90:10. x preferably has values from 3 to 10.

The miscibility of the hydrophilic modifier with the polysiloxane composition is particularly good if a relatively low degree of branching of the siloxane matrix of the modifier is maintained, that is to say f>0.8(f+g+h+i) and e>0.6(d+e+i), b, c, d, g, h and i<0.2 ( a+b+c+d+e+f+g+h+i ), in particular <0.1 ( a+b+c+d+e+f+g+h+i ) and, preferably, if more than half the end groups in the siloxane matrix are to carry exclusively radicals R, that is to say a>0.5(a+b+c+d), in particular a>0.6 (a+b+c+d).

The hydrophilic modifier has good processing properties, that is to say can be mixed quickly and homogeneously with the polysiloxane composition, if the sum of a+b+c+d+e+f+g+h+i is 10 to 400, preferably 10 to 220, in particular 20 to 160.

As a result of the preparation, the hydrophilic modifier often contains small amounts of radicals Z which denote a hydroxyl group. If the hydrophilic modifier contains Si—H groups or is mixed into a component (B) containing Si—H groups, c+d must be<0.02 (a+b+c+d+e+f+g+h+i) in this case, in order to keep the evolution of hydrogen, which impairs the storage stability, low. The hydrolyzable groups Z are preferably contained in less than 10% of the siloxane units, that is to say c+d<0.1 ( a+b+c+d+e+f+g+h+i ).

Component (A) preferably comprises a composition of polysiloxanes which contains SiC-bonded $C_1$–$C_6$-alkyl radicals, in particular methyl radicals and/or phenyl radicals, and has at least 2 $C_1$–$C_6$-alkenyl radicals, which contain the aliphatic double bonds, per molecule. The preferred alkenyl radicals are vinyl radicals and allyl radicals. Preferably, one molecule contains not more than 10 alkenyl radicals.

The chain length of the polysiloxanes of component (A) preferably should not exceed 2000 Si units per molecule. Polydimethylsiloxane having terminal vinyl groups on both ends and a chain length of 40 to 1200 Si units is particularly preferred. The viscosity at 25° C. is preferably 35 to 100,000 mm$^2$/s, in particular 500 to 10,000 mm$^2$/s.

Component (A) is essentially free from Si'H groups, so that, during storage, it forms no undesirable vulcanizates due to its content of noble metal catalyst. Component (A) of the storage-stable polysiloxane composition preferably comprises, as noble metal catalysts for the vulcanization, platinum metals and/or compounds thereof, preferably platinum and/or compounds thereof. All the catalysts which have also hitherto been employed for addition of Si—H groups onto aliphatically unsaturated compounds can be employed here. Examples of such catalysts are metallic and finely divided platinum, which can be on supports, such as silicon dioxide, aluminum oxide or active charcoal, and compounds or complexes of platinum, such as platinum halides, for example $PtCl_4$, $H_2PtCl_6 \cdot 6H_2O$ and $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, in particular platinum-dininyl-tetramethyldisiloxane complexes with or without a content of detectable inorganically bonded halogen, bis-(gammapicoline)-platinum dichloride, trimethylenedipyridineplatinum dichloride, dicyclopentadieneplatinum dichloride, dimethylsulfoxydiethyleneplatinum(II) dichloride and reaction products of platinum tetrachloride with an olefin and primary amine or secondary amine or primary and secondary amine, such as the reaction product of platinum tetrachloride, dissolved in 1-octene, with secbutylamine, or ammonium-platinum complexes according to EP-B 110 370.

The platinum catalyst is preferably employed in amounts of 0.5 to 500 ppm by weight (parts by weight per million parts by weight), in particular 2 to 400 ppm by weight, in each case calculated as elemental platinum and based on the total weight of polysiloxane composition present in components (A) and (B). Most of the abovementioned platinum catalysts are active to the extent that an inhibitor which prevents premature crosslinking to give the elastomer must be added to component (A) and/or (B). Such inhibition is not necessary if, for example, ammonium-platinum complexes according to EP-B 110 370 are employed.

Inhibitors are known and are described, for example, in U.S. Pat. No. 3,933,880. Examples of these are acetylenically unsaturated alcohols, such as 3-methyl-1-butyn-3-ol, 1-ethynylcyclohexan-1-ol, 3,5-dimethyl-1-hexyn-3-ol and 3-methyl-1-pentyn-3-ol. Examples of vinylsiloxane-based inhibitors are 1,1,3,3-tetramethyl- 1,3-divinylsiloxane, and poly-, oligo- and disiloxanes containing vinyl groups.

Component (B) comprises a composition of polysiloxanes which preferably contains SiC-bonded $C_1$-$C_6$-alkyl radicals, in particular methyl radicals and/or phenyl radicals, and has at least 3 Si—H groups per molecule. Preferably, one molecule contains not more than 5 Si—H groups.

The chain length of the polysiloxanes having Si—H groups of component (B) preferably should not exceed 1000 Si units per molecule. The viscosity at 25° C. is preferably 20 to 50,000 mm$^2$/s, in particular 100 to 5000 mm$^2$/s.

Component (B) preferably additionally comprises polysiloxanes having aliphatic double bonds, which preferably have the same properties as the above polysiloxanes of component (A).

Both component (A) and component (B) can comprise, in addition to the above constituents, fillers, such as non-reinforcing fillers, that is to say fillers having a BET surface area of up to 50 m$^2$/g, such as quartz, cristobalite, diatomaceous earth, calcium silicate, zirconium silicate, montmorillonites, such as bentonires, zeolites, including molecular sieves, such as sodium aluminum silicate, metal oxide powders, such as aluminum oxides or zinc oxides or mixed oxides thereof, barium sulfate, calcium carbonate, gypsum, glass powder and powdered plastics; and reinforcing fillers, that is to say fillers having a BET surface area of more than 50 m$^2$/g, such as pyrogenically prepared silicic acid, precipitated silicic acid and silicon/aluminum mixed oxides of high BET surface area. The fillers mentioned can be rendered hydrophobic, for example by treatment with organosilanes or -siloxanes or by etherification of hydroxyl groups to alkoxy groups. It is possible to employ one type of filler, or a mixture of at least two fillers can also be employed. The total content of fillers in the two components is preferably 10 to 80% by weight.

Both component (A) and component (B) can additionally comprise pigments, such as titanium dioxide or aluminum spinels, such as cobalt/aluminum spinel. The preferred total content in the two components is not more than 10% by weight.

Both component (A) and component (B) can comprise additives for particular purposes, in addition to the above constituents. Suitable additives are fungicides, bactericides, algicides, microbicides, odiferous substances, flavoring substances, corrosion inhibitors and, although not preferred, organic solvents. Components (A) and (B) in each case preferably comprise additives in amounts of 0.001 to 1% by weight, in particular 0.01 to 0.1% by weight.

The content of hydrophilic modifier is preferably 0.1 to 15, in particular 1 to 10% by weight, based on the total weight of components (A) and (B).

The ratios of the amounts of components (A) and (B) are preferably chosen so that they can be metered in and mixed quickly and easily. For example, the ratio of the amounts of 1:5 to 5:1 is very advantageous.

For the preparation of the hydrophilic modifier of the general formula (I) which is used according to the invention and is free from noble metal catalysts, the starting substance is preferably a silane of the general formula III $$R^1RSiZ_2 \qquad (III)$$

in which $R^1$, R and Z have the meanings given in the case of formula (I), which is distilled before the reaction in order to remove the noble metal catalyst required for the preparation of the silane. The silane of the general formula III is volatile enough for this purpose. Preferably, however, x has values from 3 to 10 and R denotes methyl or ethyl radicals.

Starting compounds and by-products of the silane III which contain Si—H groups or double bonds are also removed by the distillation.

In the following general formulae III, IV, V and VI, , $R^1$ R and Z have the meanings given in the case of formula (I), j denotes an integer from 2 to 2000 and k denotes an integer from 3 to 6.

The hydrophilic modifier used according to the invention can be prepared by silane cohydrolysis, as described in DE-A-1 519 412 (in this context, compare also W. Noll, "Chemie und Technologie der Silicone" (Chemistry and Technology of the Silicones), Verlag Chemie, Weinheim, 2nd edition, 1968, page 163 et seq.). The hydrophilic modifier which contains silicon-bonded radicals having aliphatic double bonds is preferably prepared in a manner which is known per se by mixed hydrolysis or mixed condensation of a monomeric, distilled silane of the general formula III with other hydrolyzable silanes containing silicon-bonded radicals having aliphatic double bonds, and silanes of the general formula IV $$R_2SiZ_2 \qquad (IV)$$

and/or siloxanes of the general formula V $$HO(SiR_2O)_jH \qquad (V)$$

and/or cyclic siloxanes of the general formula VI $$(SiR_2O)_k \qquad (VI)$$

The hydrophilic modifier containing Si—H groups is preferably prepared in a manner which is known per se by mixed hydrolysis or mixed condensation of a monomeric, distilled silane of the general formula III with other hydrolyzable silanes which contain silicon-bonded hydrogen, and silanes of the general formulae IV and if appropriate V and VI.

The hydrophilic modifier which contains Si—H groups and additionally radicals having aliphatic double bonds is preferably prepared in a manner which is known per se by mixed hydrolysis or mixed condensation of a monomeric, distilled silane of the general formula III with other hydrolyzable silanes which contain silicon-bonded hydrogen atoms, other hydrolyzable silanes which contain silicon-bonded radicals having aliphatic double bonds, and silanes of the general formulae IV and if appropriate V and VI.

The mixed condensation or mixed hydrolysis to prepare the hydrophilic modifier can be carried out in the presence of an acid condensation catalyst. Phosphorus nitride chlorides are preferred acid condensation catalysts for this. These compounds, which are used as such or in the form of their reaction products, are all essentially built up from phosphorus, nitrogen and chlorine atoms. They are also called phosphorus nitride dichloride, phosphorus nitride chloride and phosphorus nitrite chloride. These compounds are attributed the formulae, inter alia, $(PNCl_2)_x$, $Cl_3PNPCl_2NPCl_3PCl_6$ and $Cl_3PNPCl_3PCl_6$.

Phosphorus nitride chlorides, and in particular especially those which are accessible by reaction of phosphorus pentachloride with ammonium chloride, are preferably used in the process for the preparation of the hydrophilic modifier. These are, in particular, phosphorus nitride chlorides which are obtainable by reaction of 400 parts by weight of phosphorus pentachloride with 130 parts by weight of ammonium chloride (in accordance with Berichte der deutschen chemischen Gesellschaft, Volume 57, 1924, page 1345), and/or by reaction of two tool of phosphorus pentachloride with one tool of ammonium chloride (in accordance with U.S. Pat. No. 3,839,388). Phosphorus nitride chlorides of the type mentioned last are preferred.

The acid condensation catalyst is preferably added as a solution in one of the solvents listed below.

The preparation of the hydrophilic modifier according to the invention can be carried out in the presence or in the absence of solvents. If solvents are used, solvents or solvent mixtures having a boiling point or boiling range of up to 120° C. under 0.1 MPa are preferred. Examples of such solvents are ethers, such as dioxane, tetrahydrofuran, diethyl ether and diethylene glycol dimethyl ether; chlorinated hydrocarbons, such as methylene chloride, chloroform, carbon tetrachloride, 1,2-dichloroethane, 1,2,3-trichloropropane and trichloroethylene; hydrocarbons, such as pentane, n-hexane, hexane isomer mixtures, heptane, octane, wash benzine, petroleum ether, benzene, toluene and xylenes; or mixtures of these solvents.

The term solvent does not mean that all the reaction components must dissolve in this. The reaction can also be carried out in a suspension or emulsion of one or more reaction partners. The reaction can also be carried out in a solvent mixture having a miscibility gap, at least one reaction partner in each case being soluble in each of the mixed phases.

The use of the composition of phosphorus nitride chloride, surfactant as a solubilizing agent, and halogen-free solvent described in DE-A-3 903 137 (J. Schuster et al.; laid open on 16.8.1990 for Wacker-Chemie GmbH, DE) is particularly preferred.

The storage-stable polysiloxane compositions according to the invention can be used as dental impression compositions for exact copying of the surface in the oral cavity and for duplicating dental dentition models. They can also be used for impressions of other parts of the body, such as the auditory canal, and for all purposes for which silicone elastomers having hydrophilic properties are advantageous, for example for contact lenses, prosthesis or implants, and non-medical purposes.

In the following examples, unless stated otherwise in each case, a) all the amounts given are based on the weight;
b) all the pressures are 0.10 MPa (absolute);
c) all the temperatures are 25° C.
d) Me denotes the methyl radical
e) vinyl polymer 1 denotes polydimethylsiloxane with $\alpha,\omega$-vinyl groups and having a viscosity of about 7000 m²/s, measured by the Brookfield method at 25° C.
f) Crosslinking agent denotes anhydrous diorganopolysiloxane of dimethylsiloxane units and methylhydrosiloxane units which contains dimethylhydrosiloxane units as terminal units, wherein 10 dimethylsiloxane units are present per methylhydrosiloxane unit, and having a viscosity of 150 mPas at 25° C.;
g) Catalyst denotes a Pt-1,3-di-vinyl-1,1,3,3-tetramethylsiloxanyl complex
h) Inhibitor denotes a dimethylsiloxane having on average 5 to 10 dimethylsiloxane units and $\alpha,\omega$-vinyl groups.

EXAMPLES

Example 1: Preparation according to the invention of a hydrophilic modifier (modifier 1)

a) Silane synthesis:

A mixture of 1000 g of a polyglycol ether of the average formula:

$$H_2C=CHCH_2(OC_2H_4)_4OMe$$

Polyglycol AM 250 (from Hoechst AG) and 14.6 g of a 1% strength solution of bis(1,1,3,3-tetramethyl-1,3-divinyldisiloxane)platinum complex in hexane (=100 ppm of Pt) was reacted with 460 g of dichloromethylsilane at 70° C. After the volatile constituents had been distilled off at 50° C./4 mbar, 1326 g of a yellowish oil remained as a residue, and were reacted with 1440 g of isopropanol. Distillation up to 200° C./2 mbar gave 646 g of a yellowish liquid having the average formula:

$$H_3C((CH_3)_2CHO)_2Si(CH_2)_3(OC_2H_4)_4OMe$$

Silane 1 b) Equilibration (mixed condensation):

0.54 g of a 25% strength solution of phosphorus nitrile chloride ("PNCl$_2$") in 1,2,3-trichloropropane was added to 153 g of a polydimethylsiloxane containing terminal vinyldimethyl groups and having a chain length of about 220 Me$_2$SiO units (viscosity 1000 mPas; from Wacker-Chemie GmbH), and 2.6 g of dimethylvinylchlorosilane at room temperature, and the mixture was heated up to 100° C., while stirring. 116 g of the silane 1 prepared according to a) were metered in at 100° C. in the course of 1.5 hours, while stirring. The mixture was then stirred at 100° C. for one hour. After hydrolysis with 63 g of water, the volatile constituents were distilled off. 210 g of a red-brown, clear oil having a viscosity of 100mm$^2$/s, which, according to elemental analysis (X-ray fluorescence), contained no detectable amounts of platinum, remained as the residue. According to $^{29}$Si- and $^1$H-NMR spectra, the average formula of the hydrophilic modifier 1 thus obtained was $$[H_2C=CH-SiMe_2O_{1/2}]_{1.88}[SiMe_2OiPr]_{0.12}[SiMe_2O_{2/2}]_{44}$$
$$[SiR^1MeO_{2/2}]_{7.5} \text{ where } R^1=(CH_2)_3(OC_2H_4)_4OMe$$

Example 2: Preparation according to the invention of a hydrophilic modifier (modifier 2)

a) silane synthesis:

2,688 g of a polyether of the average formula:

$$H_2C=CHCH_2(OC_2H_4)_6OMe$$

Arlypon AL 6 (methylareal) (from Hoechst AG) were reacted with 1072 g of diethoxymethylsilane in the presence of 0.67 g of platinum tetrachloride (=100 ppm of Pt) at 70° C. Distillation up to 200° C./2 mbar gave 2624 g of a silane of the average formula:

$$H_3C((CH_3CH_2O)_2Si(CH_2)_3(OC_2H_4)_6OMe \text{ Silane 2}$$

b) Equilibration: 341 g of octamethylcyclotetrasiloxane, 12.3 g of chlorodimethylvinylsilane and 262 g of silane 2 were equilibrated in the presence of 2.2 ml of a 25% strength solution of PNCl$_2$ in 1,2,3-trichloropropane at 80° C. After addition of 139 g of water, all the volatile constituents were distilled off up to 120° C. under normal pressure. 476 g of an oil having a viscosity of 200 mm$^2$/s were obtained as the residue. According to $^{29}$Si— and $^1$H-NMR spectra, the average formula of the hydrophilic modifier 2 thus obtained was:

$$[H_2C=CH-SiMe_2O_{1/2}]_2[SiMe_2O_{2/2}]_{39}[Sir^1MeO_{2/2}]_{12} \text{ where } R^1=(CH_2)_3(OC_2H_4)_6OMe$$

Example 3: Preparation, not according to the invention, of a hydrophilic modifier (modifier 3)

A solution of 336 g of a polyether of the average formula:

$$H_2C=CHCH_2(OC_2H_4)_6Ome$$

Arylpon AL 6 (methylated) (from Hoechst AG)

in 50 ml of toluene was reacted with 1115 g of a polysiloxane of the average formula:

$$[Me_3SiO_{2/2}]_2[SiMe_2O_{2/2}]_{51}[SiHMeO_{2/2}]_9$$

in the presence of 145 mg of hexachloroplatinic acid at 80° C. After the highly volatile constituents had been stripped off in vacuo and the residue had been filtered over 30 g of active charcoal and 40 g of silica gel, g of a red-brown oil to which, according to $^1$H— and $^{29}$Si-NMR spectra, the following average formula could be assigned:

$$[Me_3SiO_{2/2}]_2[SiMe_2O_{2/2}]_{51}[SiR^1MeO_{2/2}]_9 \text{ where } R^1=(CH_2)_3(OC_2H_4)_6OMe$$

remained. The viscosity was 210 mm$^2$/s.

An Si—H residual content of 0.35 mol % could be determined by $^1$H-NMR spectroscopy. According to elemental analysis, the oil contained 65 ppm of platinum.

Example 4: Preparation of a "light body" dental composition according to the invention Component (A).

In a stainless steel planetary mixer which could be evacuated and had a capacity of 6 l and an average stirring speed of 150 revolutions per minute, 1890 g of vinyl polymer 1 and 30 g of hydrophilic modifier 2 (corresponds to 1% by weight) were mixed with 840 g of quartz flour having a particle size of 1–30 μm (from Quarzwerke Frechen)

60 g of Aerosil R 972 (from Degussa AG)

120 g of calcined kieselguhr having a porous structure and of particle size 1–20 μm (from Ceca S. A.)

10 g of chromium oxide green pigment and 6 g of TiO$_2$ pigment and the mixture was processed to a homogeneous, self-leveling composition in the course of 60 minutes.

Thereafter, 36 g of catalyst and 3 g of inhibitor were also added. The total mixture was stirred for 10 another further 15 minutes under a reduced pressure of 50–100 mbar.

Component B

In a stainless steel planetary mixer which could be evacuated and had a capacity of 6 l and an average stirring speed of 150 revolutions per minute, 1250 g of vinyl polymer 1

150 g of hydrophilic modifier 2 (corresponds to 4.91% by weight) and 450 g of crosslinking agent were mixed with 960 g of quartz flour having a particle size of 1–30 μm (from Quarzwerke Frechen)

120 g of Aerosil R 972 (from Degussa AG)

90 g of calcined kieselguhr having a porous structure and with a particle size of 1–20 μm (from Ceca S. A.) and 36 g of chromium oxide green pigment, and the mixture was processed to a homogeneous self-leveling composition in the course of 60 minutes.

The mixture was subsequently stirred for a further 15 minutes under a reduced pressure of between 50 and 100 mbar.

Example 5: Preparation of a "medium body" dental composition according to the invention Component (A)

In a stainless steel planetary mixer which could be evacuated and had a capacity of 6 l and an average stirring speed of 150 revolutions per minute, 1530 g of vinyl polymer 1

30 g of hydrophilic modifier 2

1260 g of quartz flour having a particle size of 1–30 μm (from Quarzwerke Frechen)

60 g of Aerosil R 972 (from Degussa AG)

108 g of calcined kieselguhr having a porous structure and with a particle size 1–20 μm (from Ceca S. A.) and 0.15 g of Co/Al spinel pigment were mixed, and the mixture was processed to a homogeneous, pasty composition in the course of 60 minutes.

Thereafter, 36 g of catalyst and 3 g of inhibitor were also added. The total mixture was stirred for another 15 minutes under a reduced pressure of 50–100 mbar.

Component B

In a stainless steel planetary mixer which could be evacuated and had a capacity of 6 l and an average stirring speed of 150 revolutions per minute, 1200 g of vinyl polymer 1

150 g of hydrophilic modifier 2

360 g of crosslinking agent 1020 g of quartz flour having a particle size of 1–30 μm (from Quarzwerke Frechen)

150 g of Aerosil R 972 (from Degussa AG)

90 g of calcined kieselguhr having a porous structure and with a particle size of 1–20 82 m (from Ceca S. A.) and 6 g of $TiO_2$ pigment and 40 g of Co/Al spinel pigment were mixed, and the mixture was processed to a homogeneous pasty composition in the course of 60 minutes. It was then stirred for 15 minutes under a reduced pressure of 50–100 mbar.

Example 6

Components A and B were prepared as in Example 4, but instead of the hydrophilic modifier 2 prepared according to the invention, the hydrophilic modifier 3, which was not prepared according to the invention, was used.

Example 7

Components A and B were prepared as in Example 5, but instead of the hydrophilic modifier 2 prepared according to the invention, the hydrophilic modifier 3, which was not prepared according to the invention, was used.

Example 8

In Example 5, 5 ppm of Pt were added to component B in the form of hexachloro-platinic acid (=0.05 g of $H_2PtCl_6$).

Example 9

The results of investigations presented below provide experimental evidence of the superiority of impression preparations I and II according to the invention in comparison with preparations corresponding to the prior art (impression preparations III and IV) in respect of the change in wetting properties of these impression preparations in contact with aqueous systems (sterilization).

The silicone impression preparations I, II, III and IV were mixed in the prescribed mixing ratio of components (A):(B)=1:1 homogeneously with one another and then introduced into cylindrical stainless steel molds (height: 6 mm, diameter: 35 mm), such that it was possible to remove them from the mold as cylindrical vulcanizates after a few minutes at room temperature.

The vulcanizate samples of preparations I, II, III and IV were halved along their diameter perpendicularly to the circular surface, one drop of distilled water was placed on the surface and the water contact angle was measured with the aid of a microscope goniometer at a time interval of 30 seconds and 3 minutes after application of the drop of water. The drops of water were then absorbed from the vulcanizate surface with a little cellulose, and vulcanizate samples I, II, III and IV were subjected to comparable sterilization conditions (storage at room temperature in a 1.37% strength aqueous $KClO_3$ solution for 6 hours). After the sterilization, the vulcanizate samples were dried with cellulose again, a drop of distilled water was placed on each of their surfaces and the samples were again subjected to comparative measurement of the water contact angle using a microscope goniometer.

The results of this investigation are summarized as the means of in each case 6 test specimen halves in the following Table I, and demonstrate that preparations I and II of the storage-stable polysiloxane compositions according to the invention in Examples 4 and 5 show, in contrast to preparations III and IV, which are not according to the invention, no extraction phenomena at all after sterilization with aqueous media.

The microscope goniometer carries the designation NRL C. A. Goniometer, model No. 100–230 from Ramé-Hart Inc., USA.

TABLE I

| Preparation | Viscosity in accordance with ADA 19[1] | Measurement values before sterilization Water contact angle | | Measurement values after sterilization Water contact angle | |
| --- | --- | --- | --- | --- | --- |
| | | 30 sec | 3 min | 30 sec | 3 min |
| I according to the invention Example 4 | Low | 66° | 46° | 66° | 47° |
| II according to the invention Example 5 | Medium | 63° | 45° | 63° | 45° |
| 2 not according to the invention | Low | 64° | 44° | 63° | 62° |
| 3 not according to the invention | Medium | 100° | 61° | 103° | 75° |

[1] American Dental Association, specification No. 19
2 III: Express; Light Body Regular Set; from 3M Company
3 IV: Unosil S; from De Trey Dentsply GmbH Example 10: Investigation of the storage stability of the dental compositions from Examples 4 to 8

The results are in each case shown in Table II.

a) Measurement of the consistency in accordance with ADA 19

Components A and B and the 1:1 mixtures of components A and B were stored at room temperature (RT) for 1 day or at 70° C. for 7 days and then investigated in accordance with specification No. 19 of the 10 American Dental Association (ADA 19): A volume of 0.50 ml of mixture was placed on a glass plate covered with polyethylene or Cellophane. After 1½ minutes, 0.5 ml of material was covered with a polyethylene or Cellophane platelet, and a glass plate of 75±5 g plus a 500 g weight. 12 minutes after the start of mixing, the load (glass plate and 500 g weight) is removed and the largest and smallest diameters are measured. The value for the consistency is calculated from the average of three determinations and rounded up or down to the nearest millimeter.

b) Measurement of the Dot life

The components were mixed in a ratio of 1:1 in a conical pot life cup (PL cup) using a spatula. The timing was started at the same time as the start of mixing. The mixing operation was carried out uniformly and intensively and lasted 45 seconds. After the mixing, the mixing movement was continued slowly.

The PL was reached when processing of the product was no longer possible.

c) Measurement of the water contact angle

Components A and B were vulcanized in a ratio of 1:1 according to Example 9 and investigated.

d) Shore hardness of the vulcanized impression preparations

The 1:1 mixtures were vulcanized completely at RT for 15 minutes and then investigated in accordance with DIN 53505.

e) Visual evaluation of the dental compositions

Components A and B were mixed in a ratio of 1:1 for 45 seconds and then evaluated visually.

has at least two $C_1$–$C_6$-alkenyl radicals per molecule and is essentially free of Si—H groups, and a noble metal catalyst, (B) a composition which is free of noble metal catalysts and contains polysiloxanes having Si-C bonded $C_1$–$C_6$-alkyl radicals and/or phenyl radicals, wherein the polysiloxane has at least three Si—H groups per molecule and optionally a polysiloxane composition having Si-C bonded $C_1$–$C_6$-alkyl radicals and/or phenyl radicals, wherein the optional polysiloxane has at least two $C_1$–$C_6$-alkenyl radicals per molecule, and a hydrophilic modifier of the general formula $$[R_3SiO_{1/2}]_a[R^1R_2SiO_{1/2}]_b[ZR_2SiO_{1/2}]_c[ZRR^1SiO_{1/2}]_d[RR^1SiO_{2/2}]_e \\ [R_2SiO_{2/2}]_f[SiO_{4/2}]_g[RSiO_{3/2}]_h[R^1SiO_{3/2}]_i \quad (I)$$

in which the radicals

R denote hydrogen atoms or identical or different monovalent, optionally halogen-substituted $C_1$–$C_{12}$-hydrocarbon radicals bonded via SiC, in which at least one of the radicals R contains an aliphatic double bond or denotes a hydrogen atom;

$R^1$ denotes the general formula II $$E[OY]_xR^2 \quad (II)$$

in which E denotes a single bond or a $C_1$–$C_6$-alkylene radical, Y denotes identical or different $C_1$–$C_4$-alkylene radicals, $R^2$ denotes a hydroxyl group or a $C_1$–$C_6$-alkoxy or $C_1$–$C_6$-oxycarbonylalkyl radical and x has values from 1 to 20; and Z has the meanings of $R^2$ or denotes a halogen atom; with the proviso that a, b, c and d in each case independently of one another have values from 0 to 8, the sum of a+b+c+d is 2 to 8, the sum of a+b+c+d+e+f+g+h+i is 10 to 400 and the ratio of the sums of a+b+f+g+h: b+d+e+i is 100:1 to 1:1, wherein the hydrophilic modifier is present in component (A) or (B) or both (A) and (B) with the proviso that a

TABLE II

| Consistency (mm) in accordance with ADA 19 | Example 4 | | Example 5 | | Example 6 | | Example 7 | | Example 8 | |
|---|---|---|---|---|---|---|---|---|---|---|
| | RT | 7d/ 70° C. | RT | 7d/ 70° C. | RT | 7d/ 70° C. | RT | 7d/ 70° C. | RT | 7d/ 70° C. |
| a) Component A | 45 | 43 | 44 | 43 | 45 | 37 | 44 | 35 | 44 | 44 |
| Component B | 45 | 46 | 45 | 44 | 45 1) | | 45 2) | | 45 3) | |
| Component A + B | 39 | 38 | 34 | 32 | 39 | | 34 | | 33 | |
| b) Pot life (seconds) | 210 | 205 | 210 | 200 | 200 | | 210 | | 200 | |
| c) water contact angle after 3 minutes | 46° | 46° | 45° | 45° | 46° | | 45° | | 45° | |
| d) Shore hardness after 15 min., DIN 53505 | 38 | 40 | 51 | 52 | 38 | | 51 | | 51 | |
| e) Visual evaluation | homogeneous self-leveling composition | as at RT | homogeneous pasty composition | as at RT | homogeneous self-leveling 4) composition | | homogeneous pasty composi- 5) tion | | homogeneous pasty composition | mostly vulcanized composition |

1), 2), 3) not measurable since vulcanizate contents were present
4), 5) mostly vulcanized composition
7d/70° C. = storage of the components for 7 days at 70°C. in a drying cabinet

We claim:

1. A storage-stable polysiloxane composition which gives permanently water-wettable elastomeric vulcanizates, consisting essentially of separately stored components;

(A) a polysiloxane having SiC-bonded $C_1$–$C_6$-alkyl radicals and/or phenyl radicals wherein the polysiloxane hydrophilic modifier having SiH- groups can only be present in component (B).

2. A storage-stable polysiloxane composition as claimed in claim 1, wherein a portion of the hydrophilic modifier containing radicals having aliphatic double bonds is present in both component (A) and (B).

3. A storage-stable polysiloxane composition as claimed in claim 1, wherein the ratio of a+c+f+g+h+:x(b+d+e+i) is 60:40 to 90:10.

4. A storage-stable polysiloxane composition as claimed in claim 1, wherein x has a value from 3 to 10.

5. A storage-stable polysiloxane composition as claimed in claim 1, wherein f>0.8(f+g+h+i), e>0.6(d+e+i) and b, c, d, g, h and i<0.2(a+b+c+d+e+f+g+h+i).

6. A storage-stable polysiloxane composition as claimed in claim 1, wherein a<0.5(a+b+c+d).

7. A dental impression composition comprising a storagezstable polysiloxane composition as claimed in claim 1.

8. A process for the preparation of a storage-stable polysiloxane composition as claimed in claim 1, where in a first step a silane of the general formula $$R^1RSiZ_2 \qquad (III)$$

where

R is a hydrogen atom or an identical or different monovalent, optionally halogen-substituted $C_1$–$C_{12}$-hydrocarbon radical bonded via SiC, R1 has the general formula $$E[OY]_xR^2 \qquad (II)$$

where

E is a single bond or a $C_1$–$C_6$-alkylene radical,

Y is an identical or different $C_1$–$C_4$-alkylene radical

R2 is a hydroxyl group, $C_1$–$C_6$-alkoxy radical or a $C_1$–$C_6$-oxycarbonyl alkyl radical, and x has a value from 1 to 2, and Z has the meaning of R2 or is a halogen atom;

is distilled in order to remove any noble metal catalyst in a second step the silane of formula (III) is hydrolyzed or condensed in the absence of a noble metal catalyst with silanes containing silicon-bonded hydrogen atoms and/or silicon-bonded radicals with aliphatic double bonds and silanes of the general formula $$R_2SiZ_2 \qquad (IV)$$

siloxanes of the general formula $$OH(SiR_2O)_jH \qquad (V)$$

cyclic siloxanes of the general formula $$(SiR_2O)_k \qquad (VI)$$

or mixtures thereof where in the general formula (IV), (V) and (VI) R and Z have the meanings given for formula III, j has a value from 2 to 2000, and k is an integer from 3 to 6, to give a hydrophilic modifier, and in a third step, the hydrophilic modifier is mixed with component (A) or (B) or both (A) and (B) with the proviso that a hydrophobic modifier having Si—H groups can only be mixed with component (B).

* * * * *